US011998337B2

(12) United States Patent
Cantwell et al.

(10) Patent No.: US 11,998,337 B2
(45) Date of Patent: Jun. 4, 2024

(54) REMOTE CONTROL MODULE FOR INSTRUMENTS

(71) Applicant: Medtronic Xomed, Inc., Jacksonville, FL (US)

(72) Inventors: Matthew L. Cantwell, Orange Park, FL (US); Wenjeng Li, St. Johns, FL (US); Kevin L. McFarlin, St. Johns, FL (US); Anirudhan Narasimhan, Jacksonville Beach, FL (US)

(73) Assignee: Medtronic Xomed, Inc., Jacksonville, FL (US)

(*) Notice: Subject to any disclaimer, the term of this patent is extended or adjusted under 35 U.S.C. 154(b) by 893 days.

(21) Appl. No.: 17/029,472

(22) Filed: Sep. 23, 2020

(65) Prior Publication Data

US 2021/0000363 A1    Jan. 7, 2021

Related U.S. Application Data

(63) Continuation of application No. 15/269,051, filed on Sep. 19, 2016, now Pat. No. 10,849,517.

(51) Int. Cl.
*A61B 5/24* (2021.01)
*A61B 5/00* (2006.01)
(Continued)

(52) U.S. Cl.
CPC ............... *A61B 5/24* (2021.01); *A61B 5/389* (2021.01); *A61B 5/394* (2021.01); *A61B 5/4035* (2013.01); *A61B 5/4041* (2013.01); *A61B 5/6847* (2013.01); *A61B 5/7475* (2013.01); *A61N 1/00* (2013.01); *A61N 1/36017* (2013.01); *A61B 5/4893* (2013.01); *A61B 5/6852* (2013.01);
(Continued)

(58) Field of Classification Search
CPC ..... A61B 5/389; A61B 5/4041; A61B 5/4035; A61B 5/7475; A61B 5/0002; A61B 5/4893; A61B 2018/00839; A61B 2018/0091; A61N 1/3603; A61N 1/36034
See application file for complete search history.

(56) References Cited

U.S. PATENT DOCUMENTS

| 4,265,237 A | 5/1981 | Schwanbom et al. |
| 4,630,263 A | 12/1986 | Townsend et al. |

(Continued)

FOREIGN PATENT DOCUMENTS

| AU | 2016244152 A1 | 11/2017 |
| CA | 2957385 A1 | 2/2016 |

(Continued)

OTHER PUBLICATIONS

Japanese Office Action regarding Japanese Patent Application No. 2020-135550, dated Dec. 28, 2021.

(Continued)

*Primary Examiner* — Devin B Henson
(74) *Attorney, Agent, or Firm* — Carter, DeLuca & Farrell LLP (57) ABSTRACT

A monitoring system may include a processor and display system for displaying results from the monitoring. A user may be in a sterile field away from the processor and display system and selected input devices. A controller may be physically connected to the monitoring system from the sterile field to allow the user to control the monitoring system.

18 Claims, 4 Drawing Sheets

(51) Int. Cl.
- *A61B 5/389* (2021.01)
- *A61B 5/394* (2021.01)
- *A61B 18/00* (2006.01)
- *A61N 1/00* (2006.01)
- *A61N 1/36* (2006.01)
- *A61B 18/14* (2006.01)

(52) U.S. Cl.
CPC ............ *A61B 2018/0066* (2013.01); *A61B 2018/00839* (2013.01); *A61B 2018/0091* (2013.01); *A61B 2018/00916* (2013.01); *A61B 2018/0094* (2013.01); *A61B 18/1442* (2013.01); *A61B 2018/1452* (2013.01); *A61B 2018/146* (2013.01); *A61B 2562/225* (2013.01)

(56) References Cited

U.S. PATENT DOCUMENTS

| | | |
|---|---|---|
| 5,116,332 A | 5/1992 | Lottick |
| 5,767,791 A | 6/1998 | Stoop et al. |
| 5,921,939 A | 7/1999 | Danielsson et al. |
| 6,752,816 B2 | 6/2004 | Culp et al. |
| 7,216,001 B2 | 5/2007 | Hacker et al. |
| 7,236,822 B2 | 6/2007 | Dobak, III |
| 7,292,886 B1 | 11/2007 | Kroll |
| 7,496,407 B2 | 2/2009 | Odderson |
| 7,689,292 B2 | 3/2010 | Hadzic et al. |
| 7,789,833 B2 | 9/2010 | Urbano et al. |
| 7,987,001 B2 | 7/2011 | Teichman et al. |
| 7,993,269 B2 | 8/2011 | Donofrio et al. |
| 8,068,910 B2 | 11/2011 | Gerber et al. |
| 8,126,736 B2 | 2/2012 | Anderson et al. |
| 8,255,045 B2 | 8/2012 | Gharib et al. |
| 8,374,673 B2 | 2/2013 | Adcox et al. |
| 8,498,717 B2 | 7/2013 | Lee et al. |
| 8,515,520 B2 | 8/2013 | Brunnett et al. |
| 8,568,312 B2 | 10/2013 | Cusimano Reaston et al. |
| 8,568,317 B1 | 10/2013 | Gharib et al. |
| 8,594,779 B2 | 11/2013 | Denison et al. |
| 8,670,830 B2 | 3/2014 | Carlson et al. |
| 8,680,986 B2 | 3/2014 | Costantino |
| 8,688,237 B2 | 4/2014 | Stanislaus et al. |
| 8,805,527 B2 | 8/2014 | Mumford et al. |
| 8,886,280 B2 | 11/2014 | Kartush |
| 8,892,259 B2 | 11/2014 | Bartol et al. |
| 8,926,509 B2 | 1/2015 | Magar et al. |
| 8,956,418 B2 | 2/2015 | Wasielewski et al. |
| 8,989,855 B2 | 3/2015 | Murphy et al. |
| 9,031,658 B2 | 5/2015 | Chiao et al. |
| 9,078,671 B2 | 7/2015 | Beale et al. |
| 9,084,550 B1 | 7/2015 | Bartol et al. |
| 9,084,551 B2 | 7/2015 | Brunnett et al. |
| 9,204,830 B2 | 12/2015 | Zand et al. |
| 9,918,669 B2 | 3/2018 | Brown et al. |
| 10,039,915 B2 | 8/2018 | McFarlin et al. |
| 10,123,731 B2 | 11/2018 | Brown et al. |
| 10,368,793 B2 | 8/2019 | Brown et al. |
| 10,398,369 B2 | 9/2019 | Brown et al. |
| 10,849,517 B2 | 12/2020 | Cantwell et al. |
| 10,987,506 B2 | 4/2021 | McFarlin et al. |
| 2002/0109621 A1 | 8/2002 | Khair et al. |
| 2002/0111624 A1 | 8/2002 | Witt et al. |
| 2003/0171747 A1 | 9/2003 | Kanehira et al. |
| 2003/0181798 A1 | 9/2003 | Ai-Ali |
| 2004/0135528 A1 | 7/2004 | Yasohara et al. |
| 2005/0075067 A1 | 4/2005 | Lawson et al. |
| 2005/0075578 A1 | 4/2005 | Gharib et al. |
| 2005/0085743 A1 | 4/2005 | Hacker et al. |
| 2005/0131464 A1 | 6/2005 | Heinrich et al. |
| 2005/0149143 A1 | 7/2005 | Libbus et al. |
| 2005/0159659 A1 | 7/2005 | Sawan et al. |
| 2005/0215993 A1 | 9/2005 | Phan |
| 2005/0267529 A1 | 12/2005 | Crockett et al. |
| 2006/0025702 A1* | 2/2006 | Sterrantino ............ A61B 5/389 600/554 |
| 2006/0200219 A1 | 9/2006 | Thrope et al. |
| 2006/0241725 A1 | 10/2006 | Libbus et al. |
| 2006/0276702 A1 | 12/2006 | McGinnis |
| 2007/0083193 A1* | 4/2007 | Werneth ............... A61B 5/7445 606/41 |
| 2007/0191915 A1 | 8/2007 | Strother et al. |
| 2007/0260293 A1 | 11/2007 | Carpenter et al. |
| 2007/0270678 A1 | 11/2007 | Fadem et al. |
| 2007/0270918 A1 | 11/2007 | De Bel et al. |
| 2007/0282217 A1 | 12/2007 | McGinnis et al. |
| 2008/0051673 A1 | 2/2008 | Kong et al. |
| 2008/0077198 A1 | 3/2008 | Webb et al. |
| 2008/0183190 A1 | 7/2008 | Adcox et al. |
| 2008/0183915 A1 | 7/2008 | Iima |
| 2008/0214903 A1 | 9/2008 | Orbach |
| 2008/0218393 A1 | 9/2008 | Kuramochi et al. |
| 2008/0300650 A1 | 12/2008 | Gerber et al. |
| 2008/0306348 A1 | 12/2008 | Kuo et al. |
| 2009/0024187 A1 | 1/2009 | Erickson et al. |
| 2009/0054804 A1 | 2/2009 | Gharib et al. |
| 2009/0157141 A1 | 6/2009 | Chiao et al. |
| 2009/0177112 A1 | 7/2009 | Gharib et al. |
| 2009/0182322 A1 | 7/2009 | D'Amelio et al. |
| 2009/0182328 A1 | 7/2009 | D'Amelio et al. |
| 2009/0182330 A1 | 7/2009 | D'Amelio et al. |
| 2009/0182331 A1 | 7/2009 | D'Amelio et al. |
| 2009/0186577 A1 | 7/2009 | Ross et al. |
| 2009/0240117 A1 | 9/2009 | Chmiel et al. |
| 2009/0299439 A1 | 12/2009 | Mire et al. |
| 2010/0036280 A1 | 2/2010 | Ballegaard et al. |
| 2010/0130913 A1 | 5/2010 | Baynham et al. |
| 2010/0145178 A1 | 6/2010 | Kartush |
| 2010/0152811 A1 | 6/2010 | Flaherty |
| 2010/0152812 A1 | 6/2010 | Flaherty et al. |
| 2010/0160731 A1 | 6/2010 | Giovannini et al. |
| 2010/0168561 A1 | 7/2010 | Anderson |
| 2010/0191311 A1 | 7/2010 | Scheiner et al. |
| 2010/0280568 A1 | 11/2010 | Bulkes et al. |
| 2011/0004207 A1 | 1/2011 | Wallace et al. |
| 2011/0028860 A1 | 2/2011 | Chenaux et al. |
| 2011/0071418 A1 | 3/2011 | Stellar et al. |
| 2011/0160731 A1 | 6/2011 | Bleich et al. |
| 2011/0190596 A1 | 8/2011 | Hacker et al. |
| 2011/0230734 A1 | 9/2011 | Fain et al. |
| 2011/0230782 A1 | 9/2011 | Bartol et al. |
| 2011/0230783 A1 | 9/2011 | Bartol et al. |
| 2011/0237924 A1 | 9/2011 | McGusty et al. |
| 2011/0245647 A1 | 10/2011 | Stanislaus et al. |
| 2011/0270120 A1 | 11/2011 | McFarlin et al. |
| 2011/0270121 A1 | 11/2011 | Johnson et al. |
| 2012/0004516 A1 | 1/2012 | Eng et al. |
| 2012/0071784 A1 | 3/2012 | Melkent et al. |
| 2012/0245439 A1 | 9/2012 | Andre et al. |
| 2012/0330384 A1 | 12/2012 | Perryman et al. |
| 2013/0030257 A1 | 1/2013 | Nakata et al. |
| 2013/0090641 A1 | 4/2013 | McKinney et al. |
| 2013/0116678 A1 | 5/2013 | Koss et al. |
| 2013/0245722 A1 | 9/2013 | Ternes et al. |
| 2013/0253334 A1 | 9/2013 | Al-Ali et al. |
| 2013/0261422 A1 | 10/2013 | Gilmore et al. |
| 2013/0304059 A1 | 11/2013 | Allen, IV et al. |
| 2013/0345701 A1 | 12/2013 | Allen, IV et al. |
| 2014/0005753 A1 | 1/2014 | Carbunaru |
| 2014/0039491 A1 | 2/2014 | Bakos et al. |
| 2014/0058284 A1 | 2/2014 | Bartol et al. |
| 2014/0067007 A1 | 3/2014 | Drees et al. |
| 2014/0073985 A1 | 3/2014 | Sakai et al. |
| 2014/0074084 A1 | 3/2014 | Engeberg et al. |
| 2014/0275849 A1 | 9/2014 | Acquista |
| 2014/0275914 A1 | 9/2014 | Li et al. |
| 2014/0277259 A1 | 9/2014 | Rosenberg et al. |
| 2014/0303452 A1 | 10/2014 | Ghaffari |
| 2014/0316229 A1 | 10/2014 | Tognetti et al. |
| 2014/0336635 A1 | 11/2014 | Hart et al. |
| 2014/0364920 A1 | 12/2014 | Doan et al. |
| 2015/0012066 A1 | 1/2015 | Underwood |
| 2015/0088029 A1 | 3/2015 | Wybo |
| 2015/0112325 A1 | 4/2015 | Whitman |
| 2015/0157237 A1 | 6/2015 | Murphy et al. |

(56) References Cited

U.S. PATENT DOCUMENTS

| | | |
|---|---|---|
| 2015/0173636 A1 | 6/2015 | Mokelke et al. |
| 2015/0202395 A1 | 7/2015 | Fromentin |
| 2015/0230749 A1* | 8/2015 | Gharib ............... A61B 17/0218 600/546 |
| 2015/0238260 A1 | 8/2015 | Nau, Jr. |
| 2015/0250423 A1 | 9/2015 | Hacker et al. |
| 2016/0015299 A1 | 1/2016 | Chan et al. |
| 2016/0038072 A1 | 2/2016 | Brown et al. |
| 2016/0038073 A1 | 2/2016 | Brown et al. |
| 2016/0038074 A1 | 2/2016 | Brown et al. |
| 2016/0038225 A1 | 2/2016 | Couture et al. |
| 2016/0199659 A1 | 7/2016 | Jiang et al. |
| 2016/0206362 A1 | 7/2016 | Mehta et al. |
| 2016/0235999 A1 | 8/2016 | Nuta et al. |
| 2016/0262699 A1 | 9/2016 | Goldstone et al. |
| 2016/0270679 A1 | 9/2016 | Mahon et al. |
| 2016/0287112 A1 | 10/2016 | McFarlin et al. |
| 2016/0287861 A1 | 10/2016 | McFarlin et al. |
| 2016/0317053 A1 | 11/2016 | Srivastava |
| 2017/0202570 A1 | 7/2017 | Shelton, IV et al. |
| 2017/0202598 A1 | 7/2017 | Shelton, IV et al. |
| 2018/0078161 A1 | 3/2018 | Cantwell et al. |
| 2019/0021643 A1 | 1/2019 | Brown et al. |
| 2019/0021644 A1 | 1/2019 | Brown et al. |

FOREIGN PATENT DOCUMENTS

| | | |
|---|---|---|
| CN | 2610843 Y | 4/2004 |
| CN | 101528303 A | 9/2009 |
| CN | 101594830 A | 12/2009 |
| CN | 101594906 A | 12/2009 |
| CN | 102046098 A | 5/2011 |
| CN | 102238904 A | 11/2011 |
| CN | 102762251 A | 10/2012 |
| CN | 103608069 A | 2/2014 |
| CN | 104203129 A | 12/2014 |
| CN | 105744887 A | 7/2016 |
| EP | 1587418 A1 | 10/2005 |
| GB | 2452158 A | 2/2009 |
| JP | 2004/500217 A | 1/2004 |
| JP | 2004/503266 A | 2/2004 |
| JP | 2008508049 A | 3/2008 |
| JP | 2008/519609 A | 6/2008 |
| JP | 2008538996 A | 11/2008 |
| JP | 2009/268016 A | 11/2009 |
| JP | 2010515487 A | 5/2010 |
| JP | 2011224085 A | 11/2011 |
| JP | 2012/516205 A | 7/2012 |
| JP | 2013/503015 A | 1/2013 |
| JP | 2013/506507 A | 2/2013 |
| JP | 2013505080 A | 2/2013 |
| JP | 2013/525002 A | 6/2013 |
| JP | 2014/117328 A | 6/2014 |
| JP | 2014524279 A | 9/2014 |
| JP | 2015513988 A | 5/2015 |
| JP | 2018/514258 A | 6/2018 |
| KR | 20130052534 A | 5/2013 |
| KR | 1020130052534 | 5/2013 |
| TW | I331027 B | 10/2010 |
| WO | 95/25472 A1 | 9/1995 |
| WO | 99/37359 A1 | 7/1999 |
| WO | 01/78831 A2 | 10/2001 |
| WO | 02/082982 A1 | 10/2002 |
| WO | 03026482 A2 | 4/2003 |
| WO | 2004064632 A1 | 8/2004 |
| WO | 2006/026482 A2 | 3/2006 |
| WO | 2008/012398 A1 | 1/2008 |
| WO | 2010/090835 A1 | 8/2010 |
| WO | 2011035311 A1 | 3/2011 |
| WO | 2011041684 A2 | 4/2011 |
| WO | 2011136962 A1 | 11/2011 |
| WO | 2011/150502 A2 | 12/2011 |
| WO | 2012129574 A2 | 9/2012 |
| WO | 2013/019757 A2 | 2/2013 |
| WO | 2013/151770 A1 | 10/2013 |
| WO | 2015-069962 A1 | 5/2015 |
| WO | 2015123100 A1 | 8/2015 |
| WO | 2016/160477 A1 | 10/2016 |

OTHER PUBLICATIONS

Chinese Office Action regarding Patent Application No. 201780071018. 2, dated Mar. 24, 2022.

Japanese Office Action regarding Patent Application No. 2019-515506, dated Apr. 22, 2022.

Japanese Office Action regarding Japanese Patent Application No. 2019515506, dated Feb. 4, 2022.

Canadian Office Action regarding Canadian Application No. 3099052, dated Feb. 18, 2022.

China-Decision on Rejection, corresponding to Chinese Application No. 201780071018.2, dated Sep. 23, 2022.

Canadian Examination Report regarding Application No. 2,981,636, dated Mar. 9, 2022.

Japanese Office Action regarding Application No. 2020-134805, dated May 11, 2022.

Korean Office Action regarding Application No. 1020197010841, dated Feb. 3, 2022.

Office Action dated Nov. 10, 2020 in corresponding/related Japanese Application No. Japanese Patent Appln. No. 2017-552026.

Australian Examination Report dated Dec. 8, 2018 in corresponding/ related Australian Application No. 2016244152.

Australian Office Action dated Feb. 8, 2018 in corresponding/ related Australian Application No. 2015301110.

Canadian Office Action dated Dec. 11, 2017 in corresponding/ related Canadian Application No. 2,957,385.

Canadian Office Action dated Jul. 27, 2018 in corresponding/related Canadian Application No. 2,981,635.

Cypress Perform. SPI-based CyFi™ Transceiver Data Sheet. Cypress Semiconductor Corporation. (Jun. 25, 2009) pp. 1-45.

Examination Report dated Feb. 28, 2020 in corresponding/related Australian Application No. 2019201702.

Examination Report dated Sep. 8, 2020, in corresponding/related Australian Application No. 2019203347.

Examination Report dated Sep. 8, 2020, in corresponding/related Australian Application No. 2019203348.

Extended European Search Report dated Jul. 1, 2020 in corresponding/ related European Application No. 20176316.6.

Hurley "Physiotherapy for Sleep Disturbance in Chronic Low Pack Pain: a Feasibility Randomised Controlled Trial" BMC Musculoskeletal Disorders; 11 pages; 2010.

International Preliminary Report on Patentability dated Mar. 28, 2019 in corresponding/related International Application No. PCT/ US2017/051825.

International Preliminary Report on Patentability dated Oct. 12, 2017 in corresponding International Application No. PCT/US2016/ 023903.

International Preliminary Report on Patentability dated Oct. 12, 2017 in corresponding/related International Application No. PCT/ US2016/023910.

International Search Report and Written Opinion for PCT/US2015/ 043844 dated Jan. 12, 2016.

International Search Report and Written Opinion for PCT/US2016/ 023903 dated Sep. 19, 2016 which claims benefit of U.S. Appl. No. 14/678,485, filed Apr. 3, 2015.

International Search Report and Written Opinion for PCT/US2016/ 023910 dated Aug. 5, 2016 which claims benefit of U.S. Appl. No. 14/578,452, filed Apr. 3, 2015.

International Search Report and Written Opinion dated Nov. 29, 2017 in corresponding International Application No. PCT/US2017/ 051825.

Invitation to Pay Additional Fees dated Jun. 10, 2016 for International Application No. PCT/US2016/023903 which corresponds to U.S. Appl. No. 14/678,485, filed Apr. 3, 2015.

Japanese Office Action dated Mar. 22, 2018 in corresponding/ related Australian Application No. 2017-506854.

(56) References Cited

OTHER PUBLICATIONS

Japanese Office Action dated Nov. 26, 2018 in corresponding/related Japanese Application No. 2017-506854.
Korean Office Action dated Aug. 21, 2018 in corresponding/related Korean Application No. 10-2017-7006340.
Medtronic Xomed Inc. "APS Electrode Stimulator" Brochure, 10 pages, 2010.
Office Action dated Apr. 14, 2020 in corresponding/related Chinese Application No. 201680030207.0.
Office Action dated Apr. 2, 2020 in corresponding/related Chinese Application No. 201680030281.2.
Office Action dated Apr. 22, 2019 in corresponding/related Chinese Application No. 201580053580.3.
Office Action dated Aug. 18, 2020 in corresponding/related Brazilian Application No. BR112017002470-5.
Office Action dated Aug. 26, 2020 in corresponding/related Korean Application No. 10-2019-7012435.
Office Action dated Aug. 26, 2020 in corresponding/related Korean Application No. 10-2020-7007858.
Office Action dated Feb. 13, 2019 in corresponding/related European Application No. 15753542.8.
Office Action dated Feb. 20, 2019 in corresponding/related Korean Application No. 10-2017-7032059.
Office Action dated Feb. 26, 2020 in corresponding/related Japanese Application No. 2019-050923.
Office Action dated Feb. 5, 2020 in corresponding/related Indian Application No. 201717004436.
Office Action dated Jun. 20, 2019 in corresponding/related Canadian Application No. 2,981,635.
Office Action dated Jun. 30, 2020 in corresponding/related Chinese Application No. 201580053580.3.
Office Action dated Nov. 3, 2020, in corresponding/related Canadian Application No. 2,957,385.
Office Action dated Sep. 16, 2020 in corresponding/related Chinese Application No. 201680030207.0.
Office Action regarding Australian Patent Application No. 2016243081, dated Dec. 21, 2019.
Office Action regarding Canadian Patent Application No. 2957385, dated Dec. 12, 2019.
Office Action regarding Chinese Patent Application No. 201580053580.3, dated Jan. 7, 2020 (with English Translation).
Office Action regarding corresponding/related Japanese Patent Application No. 2017552026, dated Mar. 27, 2020.
Office Action regarding European Patent Application No. 16712713.3, dated Dec. 6, 2019.
Wustrack "Change in Physical Activity One Year after Lumbar Decompression with or without Fusion, is it Correlated to Self-Reported Outcome Scores?" Proceedings of NASS 20th Annual Meeting/the Spine Journal 5 (2005) IS-189S.
Wustrack "Physical Activity does not correlate with HRQL Scores in Patients with Degeneratie Lumbar Conditions" Proceedings of the NASS 20th Annual Meeting/the Spine Journal 5 (2005) IS-189S.
European Patent Office Brief Communication regarding Oral Proceedings, Date: Jan. 12, 2023, corresponding to European Application No. 20176316.3.
European Office Action regarding Patent Application No. 20176316.6, dated Dec. 7, 2021.
Rich Vogel, Understanding Anodal and Cathodal Stimulation, the ASNM Monitor, 2017, https://www.asnm.org/blogpost/1635804/290597/Understanding-Anodal-and-Cathodal-Stimulation.
Office Action regarding Japanese Patent Application No. 2020-134805, dated Jul. 13, 2021 with English translation.
Office Action regarding Japanese Patent Application No. 2020-135550, dated Jul. 5, 2021 with English translation.
Office Action regarding European Patent Application No. 16715204.0, dated May 21, 2021.
Chinese Office Action regarding Application No. 201780071018.2, dated Aug. 24, 2021.
U.S. Appl. No. 15/269,051, filed Sep. 19, 2016, Cantwell, et al.
U.S. Appl. No. 16/531,309, 2019-0357839, filed Aug. 5, 2019, Brown, et al.
U.S. Appl. No. 16/142,224, 2019-0021643, filed Sep. 26, 2018, Brown, et al.
U.S. Appl. No. 16/142,238, 2019-0021644, filed Sep. 26, 2018, Brown, et al.
U.S. Appl. No. 16/552,708, 2019-0380639, filed Aug. 27, 2019, Brown, et al.
U.S. Appl. No. 16/678,452, 2016-0287112, filed Apr. 3, 2015, Courtney, et al.
U.S. Appl. No. 16/027,510, 2018-0345004, filed Jul. 5, 2018, Cantwell, et al.
First Office Action—Request for the submission of an Opinion, corresponding to Korean Patent Application No. 10-2017-7032060 (corresponding to PCT/US2016/023910), dated Oct. 26, 2022.
Office Action regarding Chinese Patent Application No. 201580053580.3, dated Mar. 1, 2021.
Pre-Appeal Examination Report regarding Japanese Patent Application No. 2017-552026, dated Feb. 16, 2021.
Office Action regarding Japanese Patent Application No. 2017-552026, dated Oct. 13, 2021 (with English Translation).
Summons to Attend Oral Proceedings regarding European Patent Application No. 201763166, dated Sep. 26, 2022.
European Patent Office—Office Action corresponding to EP 17 778 021.0, dated Nov. 22, 2022.

* cited by examiner

Fig-4 ically prior art.
REMOTE CONTROL MODULE FOR INSTRUMENTS

CROSS-REFERENCE TO RELATED APPLICATIONS

This application is a continuation of U.S. application Ser. No. 15/269,051 filed on Sep. 19, 2016. The entire disclosure of the above application is incorporated herein by reference.

FIELD

The subject disclosure relates to nerve monitoring systems, and particularly to remote control of nerve monitoring systems.

BACKGROUND

This section provides background information related to the present disclosure which is not necessarily prior art.

Nerve monitoring systems such as the NIM-Response® 3.0 and/or NIM-Neuro® 3.0 nerve monitoring systems, sold by Medtronic, Inc., may be used to monitor electromyography (EMG) responses. In particular, the monitoring systems may provide stimulation at a selected nerve and a response sensed or detected at muscles remote from the location of the stimulation. Monitoring the EMG responses may be used to determine whether one or more nerves has been damaged during a select procedure. In various systems, the monitoring system may be controlled by a monitor user that is spaced apart from a procedure user and a subject. Therefore, the monitor user may require instructions from the procedure user to operate the monitoring system according to a selected use by the procedure user.

SUMMARY

This section provides a general summary of the disclosure, and is not a comprehensive disclosure of its full scope or all of its features.

A nerve monitoring system may be used to monitor the integrity of a nerve. During a procedure, a procedure user may operate and/or alter an operation of the nerve monitoring system with a remote control system provided at the procedure user. The remote control system may include hardware that can be manipulated by the procedure user at the procedure user's location. Therefore, instructions or control to the nerve monitoring system may be provided at a location remote from the monitoring system.

The monitoring system may include a processor and display system for displaying results from the nerve monitoring. The monitoring system, however, may not be immediately available for placement in a sterile field or for placement proximal to a subject. The subject may be monitored with the monitoring system for a selected procedure. The procedure user may include a surgeon. The surgeon may be sterile for the selected procedure. A remote control may be connected to a monitoring and/or stimulating instrument during a procedure. A remote control may also be connected to the surgeon and interconnected with the instrument and the monitoring system. The remote control may be sterile and appropriate for placement in the sterile field.

The remote control includes a physical connection to the monitoring system with a length of conductive material. The physical connection may include a wire (e.g. copper or aluminum wire), conductive polymer, or other appropriate conductive material. The physical connection may allow for both a signal from the remote to the monitoring system to interact with the monitoring system and/or to transmit a signal to and/or from the instrument.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

Figure 1:
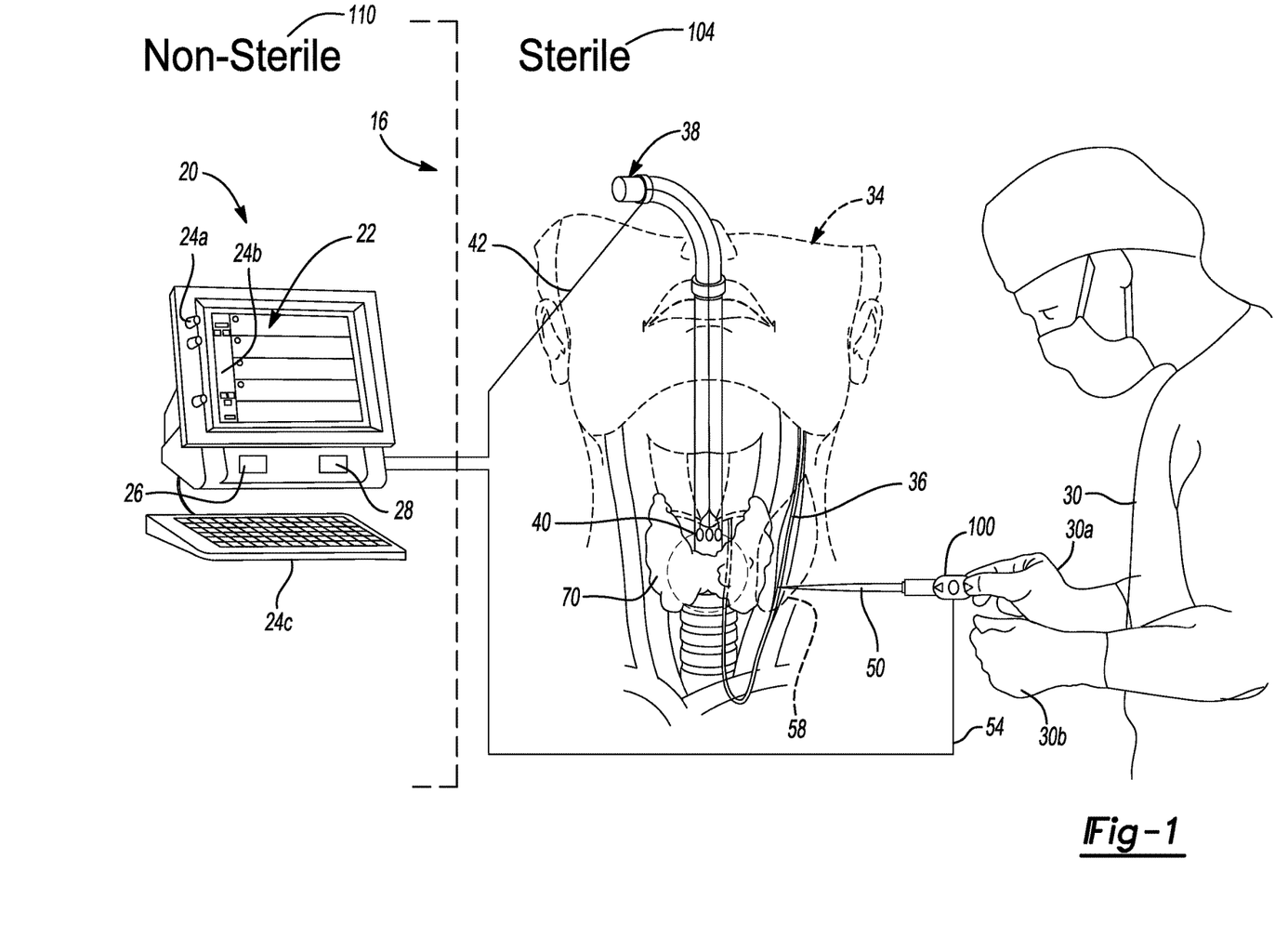
FIG. 1 is a schematic environmental view of a stimulation instrument used during a procedure.

With initial reference to FIG. 1 a monitoring system 16, such as a NIM® nerve integrity monitoring system, sold by Medtronic, Inc. having a place of business in Minneapolis, MN, is illustrated in an environmental setting. The monitoring system 16 may include a monitor assembly 20 that has a display screen or device 22 and one or more input devices. The input device may include one or more systems or structures to input commands of information such as a knob 24*a*, a touch screen 24*b*, a keyboard 24*c*, or other appropriate input devices. Input devices may also include other tactile input devices, audio input devices, visual input devices, etc.

The monitor assembly 20 may further include a processor 26 and a memory 28. It is understood that the processor 26 may access the memory 28 to execute instructions stored thereon or access other data on the memory 28. The memory 28 may include a physical memory, such as a spinning hard disk drive, solid state memory, or other appropriate types of memory. Further, the memory 28 may not be incorporated into the monitor assembly 20, but may be accessed by processor 26, such as via communications network. The processor 26 may be a general purpose processor that is operable to execute instructions for generating a selected output, as discussed further herein. The processor 26 may further include onboard memory. Moreover, the processor 26 may include a specific purpose processor such as an application specific integrated circuit (ASIC). Accordingly, the processor 26 may execute instructions stored on memory 28, which may be a non-transitory memory, to provide an output for display on the display device 22.

The monitoring system 20 may further include a stimulation portion and/or generator. The stimulation portion may be configured to generate a voltage based upon control by the processor 26. The processor 26 may execute instructions of a program stored on the memory 28 and/or control by a user 30. As discussed herein, the monitoring system 20, therefore, may be operated to generate a stimulation at or with a stimulation instrument based upon control of the user 30.

The information displayed on the display device 22 may include information selected by the user 30. The selection made by the user 30 may be desired or selected information regarding a subject 34. The subject 34 is illustrated as a human subject, but it is understood that the subject may be any appropriate living subject, including non-human subjects. Further, the monitoring system 16 may be used with non-living subjects. Non-living subjects may have systems that are selected to be monitored for selected activity, such as electrical activity, and the monitoring system 16 may be used. In selected embodiments, however, the user 30 may be performing a surgical procedure on the subject 34. The user 30, therefore, may select to monitor nerve response and/or integrity such as by monitoring electromyography (EMG) responses.

One or more stimulation or monitoring assemblies may be incorporated in the monitoring system 16 and connected with the monitor assembly 20. For example, in various procedures such as a thyroidectomy or other thyroid surgeries, monitoring of a recurrent laryngeal nerve (RLN), a vagus nerve, or other appropriate nerve 36, in the subject 30. Other or alternative nerves may also be monitored, including other selected cranial nerves and/or spinal nerves. Monitoring of the RLN may include a nerve monitoring esophageal tube 38, which may have one or more conductive electrodes 40 that are in contact with selected portions of the subject 34. The electrode 40 may be affixed to an exterior of the tube 38 and/or incorporated into the structure of the tube 38. The electrode 40 can be connected to the monitor assembly 20 via a connection 42.

In addition, other instruments may be connected to the monitor assembly 20, such as electrode assemblies, including an electrode that may send or receive periodic stimulation pulses. In various embodiments, one or more stimulation instruments 50 may be used. The stimulation instrument 50 may be connected to the monitor assembly 20 with a connector 54. The connector 54 may allow for a physical connection between the stimulation instrument 50 and the monitoring assembly 20. The connector 54 may include a conductive member (e.g. a metal wire, conductive polymer, etc.). The stimulation instrument 50 may include various instruments such as surgical instruments and the like. Examples of stimulation instruments include those disclosed in U.S. patent application Ser. No. 14/678,485 filed on Apr. 3, 2015 and U.S. patent application Ser. No. 14/678,452 filed on Apr. 3, 2015; both incorporated herein by reference.

The stimulation instrument 50 is connected with the monitor assembly 20 with the connector 54 to send and/or receive stimulation signals to the subject 34 to assist in determining whether nerve damage or other tissue damage has occurred or could occur. A surgical instrument, such as a scalpel, may be manipulated by the user 30, such as a human surgeon. The surgical instrument may not or need not be directly connected to the monitor assembly 20. The stimulation instrument 50, however, may access various portions of the subject 34, such as through an incision 58. The stimulation instrument 50 may be used to contact the nerve 36 or tissue near the nerve 36 to stimulate a response in the nerve or an EMG response at a location located a distance from the location of the stimulus application.

The monitor assembly 20 may be provided to monitor signals through or from the stimulation instrument 50 without requiring interactive stimulation or monitoring through the scalpel while performing the procedure on the subject 34. It is understood, however, that other electrode assemblies may be connected to the subject 34 as is understood by one skilled in the art. Stimulation to the subject 34 may account for a refractory period of one or more nerves.

The operation of the monitoring system and the use of the monitoring system 16 may be similar to the NIM® monitoring system sold by Medtronic, Inc., including the NIM-Response® 3.0 nerve monitoring system. In operation, the stimulation instrument 50 may be placed on contact, or at least in stimulation connection, with the nerve 36, as discussed further herein, and a signal may be transmitted along the connection 54 from the monitor system 20. The electrode 40 on the tube 38 may be a receiving electrode. It is understood, however, that other receiving electrodes may be associated and/or in contact with the subject 34.

During a procedure, user 30 may attempt or select to determine whether the integrity or continuity of the nerve 36 has been damaged during the surgical procedure. For example, various cutting or tissue moving procedures may strain or cause damage to the nerve 36 and ensuring that the nerve 36 is undamaged may be selected. The user 30, therefore, may position the instrument 50 near and/or in contact with the nerve 36. The monitoring system 16, including the stimulation system or generator of the monitoring assembly 20, may provide a stimulating voltage and/or current through the instrument 50 to attempt to evoke a response in a tissue 70. The tissue 70 may include a muscle that upon an evoked response will cause movement of the muscle 70 and/or associated tissues, such as vocal folds. The evoked response may be sensed by the EMG sensing electrodes 40 and the signal may be transmitted to the monitoring assembly 20 to allow a presentation of a message to the user 30, such as a graph, warning, auditory message (e.g. tone representing a signal received regarding the evoked EMG), or the like. The user 30 may control the monitoring assembly 20 with a remote control 100.

The remote control 100 may be positioned with the user 30, according to various embodiments, such as being connected to the instrument 50. The remote control 100 may be removably connected to the instrument 50, as discussed further herein. The remote control 100 may include switches that allow operation or control of all or certain functions of the monitoring assembly 20 while using the monitoring system 16.

The monitoring system 16 may include certain portions such as the tube assembly 38 and the instrument 50 that are configured to be used in a sterile field area 104 which is separated from a non-sterile area 110. According to various embodiments, a physical structure may be positioned to separate the sterile field 104 from the non-sterile field 110 in an operating theatre or other selected location. Nevertheless, the monitoring assembly 20, including the various inputs, such as the keyboard 24c, may not generally be accessible to the user 30 if the user 30 is in the sterile field 104. The user 30 may attempt to provide instructions to a second user in the non-sterile field 110 to operate the monitoring assembly 20, which may be inefficient. Accordingly, the remote control 100 may allow the user 30 to directly control at least portions or certain operations of the monitoring assembly 20 without moving out of the sterile field 104.

Control of the monitoring assembly 20 by the user 30 from within the sterile field 104 may allow the user 30 to make immediate decisions and configuration selections regarding operation of the monitoring system 16. Moreover, the user 30 may be a distance from the other input devices, such as the keyboard 24c, and the remote 100 may be local (e.g. within arm's length or closer) to the user 30. As discussed above, the monitoring system 16 may be used to determine or confirm integrity of the nerve 36 by providing stimulation through the nerve 36 to evoke a response in the muscle 70. Therefore, the user 30 may wish to alter a configuration or operation of the monitoring system 16 during a use of the monitoring system 16 without attempting to convey the selected change of configuration as verbal or other types of instructions to a second user or individual to attempt to reconfigure or change operation of the monitoring assembly 20 positioned in the non-sterile field 110.

One skilled in the art will understand that even if the monitoring assembly 20 is positioned in the non-sterile field 110 near the user 30, the user 30 is not able to generally interact with items in the non-sterile field 110 and immediately return to the sterile field 104 to continue the operation on the subject 34. Therefore, positioning the remote 100 in the sterile field 104 allows the user 30 to use the remote 100 in the sterile field 104 to operate the monitoring assembly 20. The conductor 54 allows a signal from the remote control 100 to be carried to the monitoring assembly 20 and/or a stimulation signal from the monitoring system 20 to be delivered through the instrument 50 to the patient 34, such as to the nerve 36.

Figure 2:
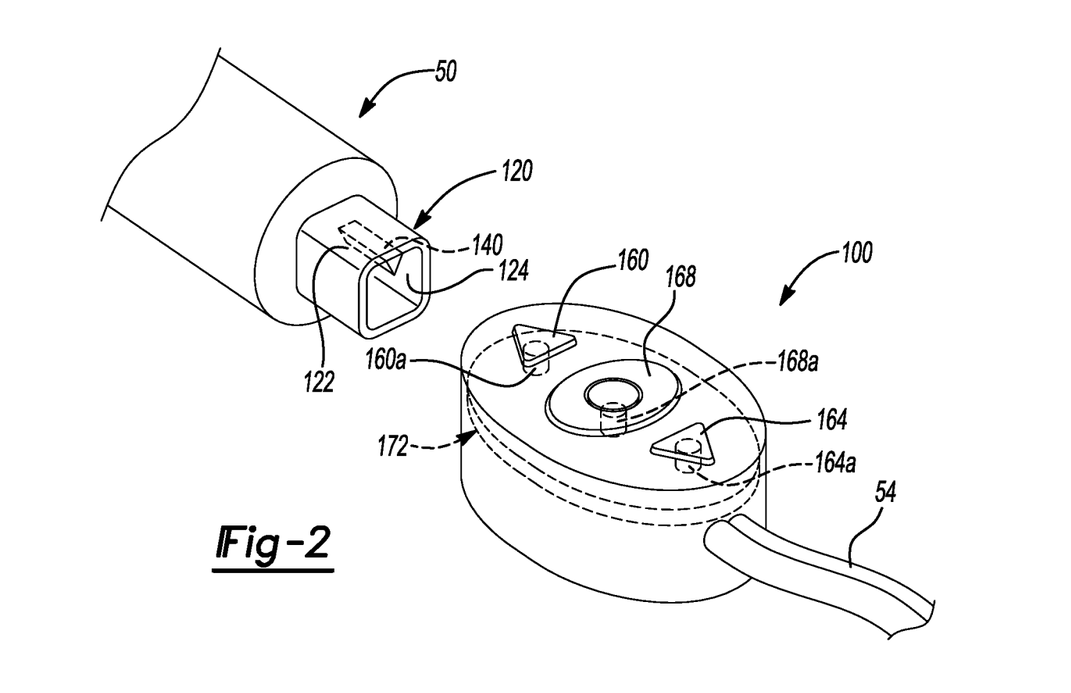
FIG. 2 is a detailed view of a remote disconnected from the instrument.
Figure 3:
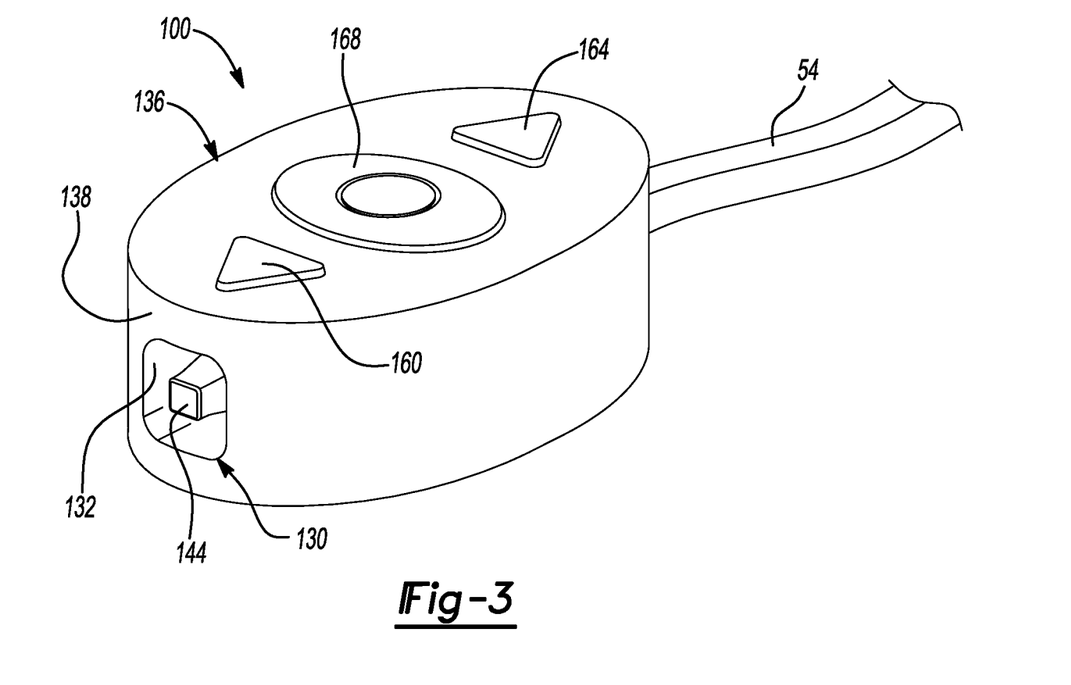
FIG. 3 is a detailed view of the connector of the remote control.

With continuing reference to FIG. 1 and additional reference to FIG. 2 and FIG. 3, the remote 100 will be discussed in greater detail. As illustrated in greater detail in FIG. 2 and FIG. 3, the remote 100 may be removably connected to the instrument 50. The controller 100, however, may be rigidly connected to the instrument 50. In various embodiments, the controller 100, when rigidly connected to the instrument 50, will not move relative to the instrument 50 until disconnected from the instrument by the user 30.

To assist in the rigid connection, the instrument 50 may include a connecting portion, such as a male connector 120 having an external wall 122 and an internal wall 124. The external wall 122 may have a non-circular geometry, such as a square shape. The square shape may assist in resisting or eliminating rotation of the controller 100 relative to the instrument 50. The remote 100, as specifically illustrated in FIG. 3, may include a mating connector having a female connector 130 having an internal wall 132. The female connector 130 may be formed as a depression within a housing 136 of the remote 100. The housing 136 may include an external wall or surface 138 into which the female connection portion 130 may be formed. The male connection portion 120 and the female connection portion 130 may form a physical and rigid connection between the instrument 50 and the remote 100. The female connector 130, therefore, may have a complementary shape to the male connector 120 to assist in maintaining rotational and axial rigid connection. The connection, however, may allow for rotation if selected, such as both connector portions being round in shape.

An electrical or conductive connection may be made via the connecting portions 120, 130 or other portions. For example, the instrument 50 may form a female conducting connection portion 140, such as with or on the internal wall 124. The internal wall 124 may include one or more conductors to connect with various portions of the instrument 50, such as providing multiple connections for a bi-polar or multi-polar stimulation. The remote 100 may include a male conductive connector 144 within the female connection 130. The male conductive connector 144 may be formed as a selected male connection, such as a banana plug or clip. The male connector 144 may make a conductive connection with the female connector 140 on the instrument 50. The male connector 144 may further be electrically connected to the conductor 54 that connects the remote 100 to the monitoring assembly 20. The conductor 54 allows for a physical connection of the remote 100 to the remote assembly 20. Therefore, the instrument 50 may be electrically and physically connected to the remote assembly 20 to allow for operation of the instrument 50 by the user 30 in the monitoring system 16.

The remote control 100 can include various control options including audio inputs, physical inputs, and the like. For example, the remote control 100 may include one or more push buttons such as a first push button 160, a second push button 164, and a third push button 168. Each of the push buttons 160, 164, and 168 may be physical buttons or members that move relative to the housing 136 to actuate a respective switch that is positioned below the button, but associated with the button on a printed circuit board (PCB) 172 positioned within the housing 136. The PCB 172 may include electrical switches 160a, 168a, 164a corresponding to the respective buttons 160, 168, and 164. The PCB 172 may include electrical connections or conductive connections from each of the switches 160a, 164a, and 168a to the conductor 54. Therefore, a signal from the respective switches 160a, 164a, and 168a may be transmitted to the monitoring assembly 20 to control and/or operate the monitoring assembly 20. It is understood that other appropriate switches may be provided such as mechanical toggle switches, touch sensitive portions (e.g., capacitive surfaces), a joystick, trackball, roller button (e.g. center rolling button on a computer mouse), or the like.

It is further understood that any appropriate number of input buttons or portions may be provided with the remote 100. Accordingly, including three buttons 160, 164, 168 are merely exemplary. Moreover, pressing or actuating more than one of the buttons at a time may operate the monitoring assembly 20 in a manner different and distinct from depressing any single one of the buttons 160, 164, 168 individually. Further, operating or depressing any one of the buttons in sequence in a selected amount of time (e.g., depressing a first button and a second button within two seconds of the first button) may operate the monitoring assembly 20 in a further different manner.

In various embodiments, the monitoring system 20 may be used to provide stimulation to the nerve 36 and receive a signal regarding an evoked response, such as in the muscle 70, such as through the contacts 40. Therefore, the user 30 may operate the remote control 100 to manually provide a stimulation pulse to the nerve 36, alter an amplitude of the stimulation pulse, alter a frequency of the stimulation pulse, or the like. According to various embodiments the remote control 100 may be operated to increase and/or decrease a stimulation current. For example, the first button 160 may be operated to increase stimulation current while the second button 164 may be operated to decrease the stimulation current. The buttons may include visual indicia to indicate a selected operation. For example, the first button 160 may be formed as an arrow or a triangle generally pointing "up" such as towards the instrument 50. The second button 164 may include a visual indication, such as an arrow or triangle pointing "down", such as away, from the instrument 50, to assist in indicating a decrease in operation. The third button 168 may be a selection button, such as a menu selection, confirmation, or other general input that may be used to switch a current operation of the monitoring assembly 20.

The remote 100 may further be used to control the monitoring assembly 20 such as to increase or decrease an audio output or message from the monitoring assembly 20. Again, the first button 160 may be used to increase the volume while the second button 164 may be used to decrease the volume. The third button 168 may be used to cycle through various controllable options, such as between increasing and decreasing stimulation current and increasing and decreasing a message volume from the monitoring assembly 20.

The remote 100 may be further used to operate to collect information or store information being received or displayed by the monitoring assembly 20. Again, as discussed above, the electrodes 40 may receive an evoked response due to a stimulation of the nerve 36. The evoked response may be displayed on the display device 22 or otherwise presented as a message to the user 30. The remote 100 may be operated to acquire or save a snapshot (e.g., a screenshot) of information currently being displayed or represented by the monitoring assembly 20. For example, the display device 22 may display a graph regarding the perceived or sensed evoked response. Acquiring, a screenshot of the display device 22 allows the user 30 to save a selected signal received by the monitoring assembly 20 from the electrodes 40. The user 30 may use the saved screenshot, such as at a later time, for comparison to a later acquired or later received signal. Further, the saved screenshot may be used to assist in training at a later period.

The remote 100 may further be used to set or control threshold limits. Threshold limits may relate to stimulation current and/or voltage. Further, the threshold limits may relate to the received responses or received signals at the electrodes 40. The control threshold limit may set an upper or lower limit regarding a waveform that is identified as the received signal by the electrodes 40.

The remote control 100 may be further operated to operate a selected system. For example, the monitoring assembly 20 may be operated with a continuous or automatic pulse system. For example, the automatic periodic stimulation (APS® Stimulation System, sold by Medtronic, Inc.) may be connected with the nerve 36. The remote control 100 may be used to operate the periodic stimulation through an automatic periodic stimulation system. For example, adjusting a stimulation current may be made, similar to that discussed above, through the electrode. Further, the APS® Monitoring System may include various features such as determining a baseline evoked response from the periodic stimulation and alarm conditions relating to deviations from the baseline. The remote control 100 may be used to control the monitoring system 20 during and/or to initiate a baseline determination (e.g., inputting a beginning and ending time for identifying a baseline, changing the volume and/or muting a presented signal (e.g. a periodic tone relating to the evoked and sensed response), changing or controlling alarm conditions regarding a deviation from the baseline, and other appropriate features of the APS® Monitoring System). Accordingly, the remote control may be used to operate various features of the monitoring assembly 20 within the monitoring system 16.

Figure 4:
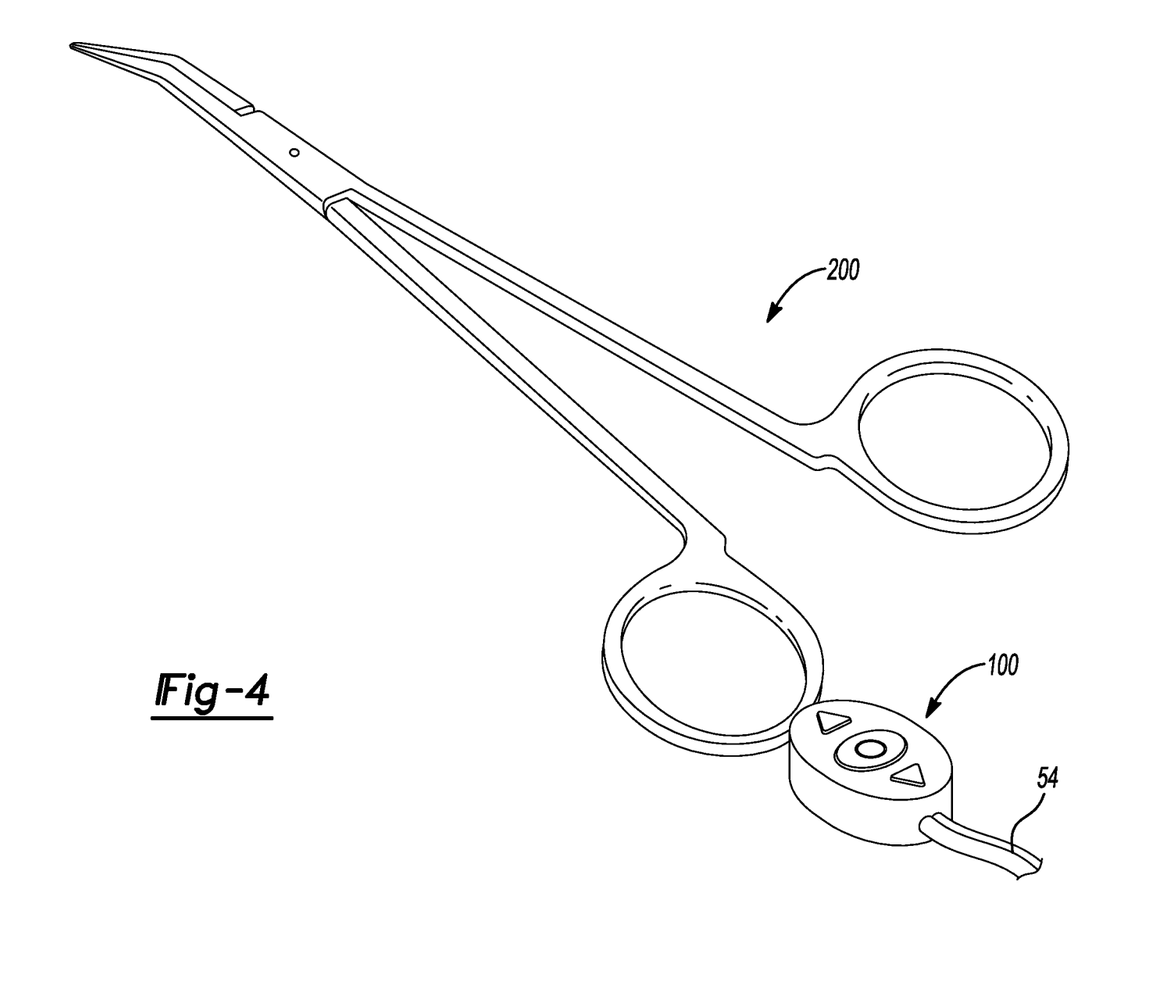
FIG. 4 is a view of the remote connected to an alternative instrument.

Turning reference to FIG. 4 it is understood that the remote 100 may be interconnected with any appropriate instrument. For example, the instrument may be a stimulating electrode forceps 200 and may include a connection similar to the male connector 120 of the instrument 50 to be interconnected with the female connection portion 130 of the remote 100. The forceps 200 may include one or more contact electrodes to contact various portions of the subject 34, such as near or at the nerve 36 and/or other tissue portions.

Nevertheless, it is understood that the remote 100 may be connected with selected instruments, such as either a single tip probe or a dual tip forceps, or other appropriate instrument. Moreover, it is understood that the remote 100 may be connected to a first instrument, disconnected from the first instrument 50, and then connected to the second instrument 200. The remote may then be disconnected from the second instrument 200 and reconnected to the first instrument 50. Further, it is understood that a kit of instruments may include any appropriate number of instruments and the remote 100 may be connected, disconnected, and reconnected to different instruments a selected number of times.

The remote 100 may be connected substantially directly to the instrument 50, 200 to allow for ease of operation of the remote by the user 30 while grasping the respective instrument 50, 200. The user 30 may use one or both hands 30a, 30b to manipulate both the instrument 50, 200 and/or the remote 100. The user 30 may use a digit of one or both hands to depress or operate the inputs, such as the buttons 160, 164, 168, to control the monitoring assembly 20. For example, only a single digit (e.g. finger of a hand) may be used to press the first button 160. As noted above, pressing the first button may increase a stimulation current.

Figure 5:
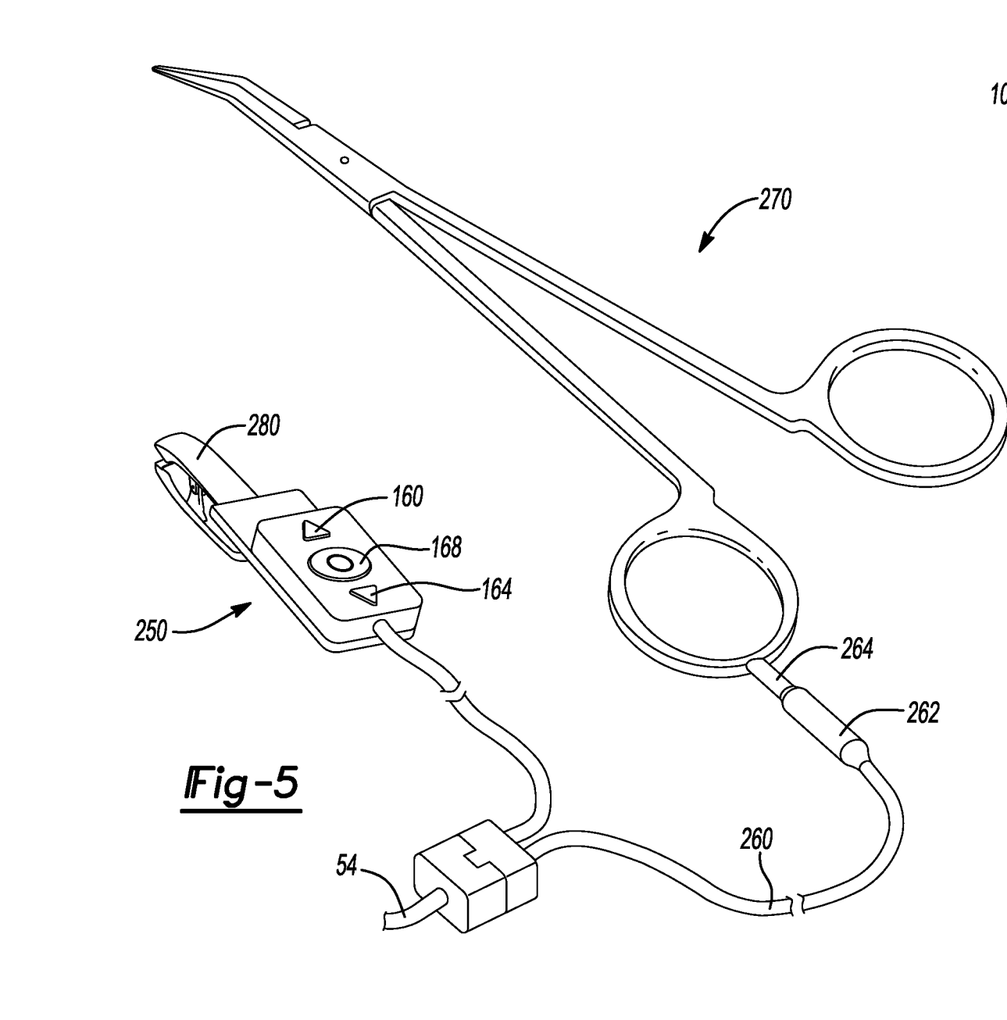
FIG. 5 is an environmental illustration of a remote control, according to various embodiments, connected with an instrument.

According to various embodiments, however, as illustrated in FIG. 5, a remote control 250 may be connected via a connector, similar to the connector 54, including an instrument connection connector 260. The instrument connection connector 260 may include a first connection portion 262 that connects to a second connection portion 264. The second connection portion 264 may extend and be connected to an instrument 270. The instrument 270 may be similar to the instrument 200, as discussed above, or may also be similar to the instrument 50 as discussed above.

The connector 260 allows the remote 250 to be positioned a distance from the instrument 270. For example, the remote 250 may be connected to a holder, such as including a clip 280. The clip 280 may be clipped to a select portion, such as a sterile draping (e.g. placed over the subject 34 or portion near the subject 34) or to a garment of the user 30, to position the remote 250 near or at the user 30 and away from the patient 34. The user 30 may then move one or more of the hands 30a, 30b to operate the remote 250.

The remote 250 may be similar or identical to the remote 100 and includes the first button 160, the second button 164, and the third button 168. Further, the remote 250 may include any appropriate input portions including those discussed above. Nevertheless, the remote 250 may be positioned at a convenient and advantageous location for operation by the user 30. The instrument connector 260 may be connected via the conductor 54 to the monitoring assembly 20 in the non-sterile field 110. The instrument connector 260 may be interconnected with the conductor 54 and/or directly connected to the monitoring assembly 20. The instrument connection portion 260 may be provided to allow for positioning of the remote 250 at a selected location remote and away from the instrument 270. Therefore, it is understood that the remotes 250 may be positioned away from the instrument 270 for operation by the user 30. The remote 100, however, may be directly connected to the selected instrument to be operated by the user 30.

It is further understood, that the remote 250 may be positioned in line with the conductor 260. The remote 250 need not be connected to the instrument 200 or instrument 270, but need not be on a separated conductor connected to the conductor 260. Thus, the remote 250 may be positioned a distance from the instrument 270, but be electrically connected thereto, such as with the conductor 260.

Further, the clip 280 need not be rigidly connected to the remote 250. For example, the clip 280 may be connected to the conductor 260. The clip 280 may then be connected to an object, such as the surgeon 30, as discussed above, and the conductor 260 would then assist in maintaining the remote 250 near the surgeon 30. Thus, the clip 280 need not be formed as a part of the remote 250.

Figure 6:
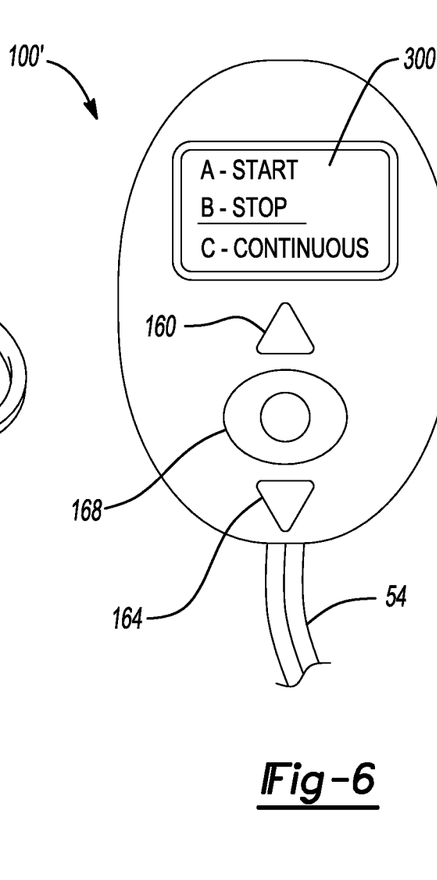
FIG. 6 is a detailed view of a remote disconnected from an instrument, according to various embodiments.

According to various embodiments, a display 300 may be included on the remote 100 or remote 250. For example, as illustrated in FIG. 6, the display 300 on a remote 100' may be viewable by the surgeon 30. The remote 100' may be substantially similar or identical to the remote 100, save for the addition of the screen 300. The screen 300 may be any appropriate display such as a liquid crystal display, light emitting diode display, etc. The display 300 may also allow for direct input from the surgeon 30 and/or display of selections that may be altered with the other switches 160, 164, and 168. Direct input may be with a touch sensitive screen while other inputs may be selected with the buttons 160, 164, 168.

The display 300 may display selected information to the surgeon 30, such as present operation of monitoring assembly 20. The present operation may include whether or not stimulation is occurring, the type of stimulation, stimulation current or voltage, etc. The display 300 may also display control options, such as START, STOP, CONTINUOUS, increase stimulation, decrease stimulation, The screen 300 may also be used on the remote to operate the monitoring assembly 20, in a manner similar to that discussed above. For example, a selected type of operation may be displayed or selected by the surgeon 30. As illustrated in FIG. 6, the display may display "STOP" or an icon related to stopping stimulation and the STOP icon may be highlighted, as selected by the user 30, with an underline. The surgeon 30 may select STOP via a touch screen or selection, such as with the buttons 160, 164, 168. The system may then operate as selected by the surgeon 30. Thus, the display 300 may be used on the remote 100' alone or in combination with the other buttons to control the monitoring assembly 20.

The display 300 may display various icons and communications based on instructions that are stored and accessed by the processor 26. For example, the processor 26 may execute instructions to display on the display 300 a selection of a command to start and stop stimulation. The user may then operate the remote 100', such as with the button 160, to select or highlight (e.g. with an underline displayed on the display 300) one of the displayed icons. The user 30 may then input a command by selecting, such as by depressing the button 168, the highlighted or selected icon. It is understood that such instructions may be incorporated into selected algorithms and instructions, as is understood by one skilled in the art.

According to various embodiments, the remote, such as the remote 100 need not be physically connected to the conductor 54 for communicating with the monitoring assembly 20. As discussed above, the conductor 54 allows a signal from the remote control 100 to be carried to the monitoring assembly 20 and/or a stimulation signal from the monitoring assembly 20 to be delivered through the instrument 50 to the patient 34, such as to the nerve 36. The remote 100, however, may include a wireless communication system or portion, such as those generally known in the art, to communicate with the monitoring assembly 20. The remote 100 may be operated, as discussed above, however, an instruction from the surgeon 30 may be communicated to the monitoring assembly 20 with a wireless or over the air (OTA) transmission. Also, transmissions from the monitoring assembly 20 regarding operation of the monitoring assembly 20 may be wireless or OTA to the remote 100. The conductor 54, or other selected conductor, may be connected to the selected instrument, such as the instrument 200, for providing the stimulation to the electrodes. Control, or at least selected control, of the monitoring assembly 20 may be with the remote 100 that is wirelessly communicating with the monitoring assembly 20.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A stimulation monitoring system to stimulate at least a portion of a patient with a stimulation instrument, comprising:
   a monitoring assembly configured to be positioned in a non-sterile field, the monitoring assembly configured to generate a stimulation voltage;
   a remote controller configured to be conductively connected to a handle of the stimulation instrument and configured to be positioned within a sterile field adjacent the patient; and
   a conductor physically connected to the monitoring assembly and the remote controller;
   wherein the remote controller includes an input to remotely control at least one operation of the monitoring assembly;
   wherein the conductor is connected between the stimulation instrument and the remote controller and between the remote controller and the monitoring assembly, wherein the remote controller is configured to be spaced apart from the stimulation instrument but adjacent the patient;
   wherein the remote controller is configured to enable the remote controller to be carried in the sterile field;
   wherein the remote controller is configured to be removably and rigidly connected to the handle of the stimulation instrument and carried by the stimulation instrument.

2. The stimulation monitoring system of claim 1, further comprising a monitor having at least one monitor electrode, the monitor configured to be positioned within the sterile field and at the patient, the monitor conductively connected to the monitor assembly to provide monitored information from the patient.

3. The stimulation monitoring system of claim 1,
wherein the monitoring assembly includes a processor configured to receive a signal from the input to control at least one operation of the monitoring assembly;
wherein the at least one operation of the monitoring assembly includes at least one of changing a stimulation period, changing a stimulation voltage, starting stimulation, stopping stimulation, capturing a screen shot, controlling a threshold limit, or changing a message volume.

4. The stimulation monitoring system of claim 1, wherein the remote controller includes a coupling member configured to enable the remote controller to be carried by the stimulation instrument in the sterile field.

5. The stimulation monitoring system of claim 1, wherein the handle is configured to be grasped by a user during stimulation of the patient.

6. The stimulation monitoring system of claim 1, further comprising:
a stimulation system configured to generate the stimulation voltage;
the stimulation instrument configured to be positioned within the sterile field near the patient.

7. The stimulation monitoring system of claim 6, wherein the input includes at least one switch;
wherein the at least one switch is configured to be operated by the user within the sterile field.

8. The stimulation monitoring system of claim 7, wherein the remote controller includes an external housing;
wherein the at least one switch includes a first portion configured to extend from the external housing to be directly engaged by digit and a second portion having a toggle switch fixed to a printed circuit board placed within the external housing;
wherein the toggle switch is configured to generate a signal that is transmitted to the stimulation system;
wherein the stimulation system includes a processor configured to receive the signal to control at least one operation of the stimulation system.

9. The stimulation monitoring system of claim 8, wherein the stimulation system includes a processor configured to receive a signal from the input to control at least one operation of the stimulation system;
wherein the at least one operation of the stimulation system includes at least one of changing a stimulation period, changing a stimulation voltage, starting stimulation, stopping stimulation; capturing a screen shot, controlling a threshold limit, or changing a message volume.

10. The stimulation monitoring system of claim 1, wherein the remote controller comprises an instrument connection connector.

11. The stimulation monitoring system of claim 10, wherein the instrument connection connector comprises a first connection portion that connects to a second connection portion of the stimulation instrument.

12. A method of monitoring a stimulation system that stimulates at least a portion of a patient with a stimulation instrument, the method comprising:
configuring a monitoring assembly to be positioned in a non-sterile field and generate a stimulation voltage;
providing a remote controller conductively connected to a handle of the stimulation instrument;
configuring the remote controller to be positioned within a sterile field adjacent the patient;
providing a conductor to be physically connected to the monitoring assembly and the remote controller; and
providing the remote controller to provide an input to remotely control at least one operation of the monitoring assembly;
wherein the remote controller is configured to be removably and rigidly connected to the handle of the stimulation instrument and carried by the stimulation instrument.

13. The method of claim 12, further comprising:
providing the conductor to be connected between the remote controller and the monitoring assembly.

14. The method of claim 13, further comprising:
configuring the remote controller to be carried by the stimulation instrument in the sterile field.

15. The method of claim 13, further comprising:
providing the stimulation instrument to be positioned within the sterile field;
providing the monitoring assembly to be positioned in the non-sterile field out of the sterile field;
providing a physical connection of the remote controller to the stimulation instrument within the sterile field;
providing a physical connection of the remote controller to the stimulation monitoring assembly in the non-sterile field; and
configuring the remote controller to control at least one operation of the stimulation system within the sterile field.

16. The method of claim 12, further comprising:
physically connecting the remote controller directly to the stimulation instrument within the sterile field including interconnecting a housing of the remote controller with the stimulation instrument.

17. The method of claim 12, further comprising:
providing the remote controller to transmit a signal with the conductor from the remote controller in the sterile field to the monitoring assembly in the non-sterile field.

18. A stimulation monitoring system to stimulate at least a portion of a patient with a stimulation instrument, comprising:
a monitoring assembly configured to be positioned in a non-sterile field, the monitoring assembly configured to generate a stimulation voltage;
a remote controller conductively connected to a handle of the stimulation instrument and configured to be positioned within a sterile field adjacent the patient, wherein the handle is configured to be held by a user within the sterile field and adjacent the patient; and
a conductor physically connected to the monitoring assembly and the remote controller;
wherein the remote controller includes an input to remotely control at least one operation of the monitoring assembly;
wherein the conductor is connected between the remote controller and the monitoring assembly, wherein the remote controller is carried by the stimulation instrument and accessible by the user;
wherein the remote controller is configured to enable the remote controller to be carried in the sterile field;
wherein the remote controller is configured to be removably and rigidly connected to the handle of the stimulation instrument and carried by the stimulation instrument.

* * * * *